United States Patent [19]

Iverson et al.

[11] Patent Number: 4,729,099
[45] Date of Patent: Mar. 1, 1988

[54] THERAPY TREATMENT PLANNING BY RADIATION DOSE DETERMINATION

[75] Inventors: Neil A. Iverson, Mentor; Robert A. Cecil, Solon, both of Ohio; Marc R. Sontag, Cherry Hill, N.J.

[73] Assignee: Picker International, Inc., Cleveland, Ohio

[21] Appl. No.: 757,071

[22] Filed: Jul. 19, 1985

[51] Int. Cl.$^4$ .................. G01T 1/02; A61N 5/10; G06F 15/42
[52] U.S. Cl. .................................................. 364/414
[58] Field of Search ................. 364/414; 378/65, 97

[56] References Cited

U.S. PATENT DOCUMENTS

| | | | |
|---|---|---|---|
| 3,871,579 | 3/1975 | Inamura | 364/414 |
| 3,987,281 | 10/1976 | Hodes | 364/414 |
| 4,455,609 | 6/1984 | Inamura et al. | 364/414 |

OTHER PUBLICATIONS

European patent publication No. 212,793, search report, based on application No. 86304579, published Mar. 4, 1987.
Mohan, R. et al., "Validity of the Concept of Separating Primary and Scatter Dose", *Med. Phys.*, vol. 12, No. 6, 1985, 726–730.
Altschuler, M. D. et al., "A Clinically Operational Method for Three-Dimensional Dose Calculations", *Phys. Med. Biol.*, vol. 30, No. 3, 1985, 217–228.
Iwasaki, A. et al., "The Differential Scatter-Air Ratio and Differential Backscatter Factor Method Combined with the Density Scaling Theorem", *Med. Phys.*, vol. 11, No. 6, 1984, 755–763.
Battista, Jerry J. et al., "Computed Tomography for Radiotherapy Planning", *Radiation Oncology-Biology-Physics*, vol. 6, 1980, 99–107.
Cunningham, J. R. et al., "Program Irreg-Calculation of Dose from Irregularly Shaped Radiation Beams", *Computer Programs in Biomedicine* 2, 1972, 192–199.
Cunningham, J. R., "Scatter-Air Ratios", *Phys. Med. Biol.*, vol. 17, No. 1, 1972, 42–51.
Day, M. J., "A Note on the Calculation of Dose in X-Ray Fields", *British Journal of Radiology*, vol. XXIII, No. 270, 1950, 368–369.
Larson, Kenneth B. et al., "Absorbed-Dose Computations for Inhomogeneous Media in Radiation-Treatment Planning Using Differential Scatter-Air Ratios", *IEEE*, 1978, 93–99.
Sontag, Marc R. et al., The Equivalent Tissue-Air Ratio Method for Making Absorbed Dose Calculations in a Heterogeneous Medium, *Radiology*, vol. 129, No. 3, 1978, 787–794.

*Primary Examiner*—Jerry Smith
*Assistant Examiner*—Clark A. Jablon
*Attorney, Agent, or Firm*—Watts, Hoffmann, Fisher & Heinke Co.

[57] ABSTRACT

A differential scatter-air ratio calculation procedure is utilized to calculate scatter contribution which when combined with primary radiation yields patient dose. The lengthy polar coordinate integration of the prior art is replaced with a rectangular coordinate integration which to an extent can be performed outside an integration loop. Beam characteristics are entered into a one dimensional matrix BWP. A second matrix RSAR includes the differential scatter air ratio for incremental regions within the patient at a certain depth and radial distance from a scatter calculation point. During a rectangular coordinate integration, a two dimensional coordinate within a patient plane determines an offset into both the one dimensional beam characteristic matrix BWP and the differential scatter-air ratio matrix RSAR. Then values are multiplied to produce a scatter contribution from the incremental region.

15 Claims, 12 Drawing Figures

THERAPY TREATMENT PLANNING BY RADIATION DOSE DETERMINATION

DESCRIPTION

1. Technical Field

The present invention relates to radiation dose calculations used in determining a radiation therapy treatment plan for a patient.

2. Background Art

When radiation is absorbed by cancerous tissue, in many instances the tissue is damaged to the point it becomes dormant and disappears. In other instances, radiation treatment is used as a follow-up measure in conjunction with radical, surgical removal of cancerous tissue. Within the past few years, computed tomography scanners have been utilized for diagnosing a patient condition and also utilized for simulating x-radiation treatment of that condition.

In an actual radiation treatment a patient is selectively irradiated by a radiation source in accordance with a precisely defined treatment plan. The radiation source produces either x-radiation or gamma radiation depending on whether an x-ray tube or radioactive element such as cobalt is used as the source. In such a therapy treatment session, the intent is that a volume containing the cancerous tissue, i.e. the tumor, receive a fatal dose of radiation and that other regions within the patient receive minimal doses to reduce the damage caused by radiation absorption.

Studies conducted on the effectiveness of radiation treatment of cancer patients indicate that radiation dose levels must be precise if the radiation treatment is to have beneficial effects. To control radiation dose at a region within the patient, prior art techniques use beam definition devices of differing shapes positioned within a radiation beam to selectively block radiation from reaching the patient. The intensity of radiation reaching the patient is also controlled. The planning of a radiation treatment for a patient is an interactive process whereby the therapist determines a desired dose for a particular patient region and then devises one or more radiation beams to irradiate that region with the prescribed dose while minimizing radiation absorption at other patient regions.

In the prior art, the task of determining desired dose and constructing an appropriate radiation beam to provide that dose is done with the aid of a computer. The computer calculates beam doses for specified conditions and allows the therapist to change those conditions to most accurately achieve a desired treatment. In the prior art, this process typically takes about one hour for each patient. This time is required for the therapist to plan a treatment, construct a beam configuration, allow the computer to calculate dosage based upon that configuration, make adjustments in the beam configuration based upon an initial calculation and once an appropriate beam is defined and confirmed, actually conduct the radiation treatment. Much of the time in a prior art radiation treatment session is spent waiting for the computer to calculate patient dose based upon user inputs.

Total radiation dose results from not only primary irradiation, i.e. radiation passing directly from a radiation source to the cancerous region but also includes a scatter contribution caused by Compton scattering of radiation from other regions in the patient. In order to accurately calculate dosage, the computer must therefore take into account direct irradiation as well as scatter contributions from other regions. This is a time consuming process and significantly slows patient through-put. This is especially true if irregualr beam geometrics are constructed using beam blocking devices.

In one prior art technique for determining absorbed dose, scatter calculations are performed using a differential scatter-air ratio technique proposed by J. R. Cunningham in two printed publications entitled "Scatter-air Ratios", Phys. Med. Biol., 1972, Vol. 17, No. 1, 42–51, and "Calculation of Dose From Irregularly Shaped Radiation Beams", Computer Programs in Biomedicine 2 (1972) 192–199. North-Holland Publishing Company. The subject matter of these two prior art references is expressly incorporated herein by reference.

In accordance with procedures disclosed in these two printed publications, scatter radiation to a particular region within a subject is calculated using an integration technique which accesses differential scatter-air ratio tables stored in the computer. Incremental scatter doses are calculated for pie shaped regions extending from the dose calculation point to the boundry of the radiation beam. This integration is performed in polar coordinates wherein a radial distance from the point of interest to the beam boundry is first determined and then used to access a scatter-air ratio corresponding to that radial distance. This prior art procedure, while theoretically correct, results in long calculation times with diminished patient through-put.

DISCLOSURE OF THE INVENTION

A principal feature of the invention is more rapid therapy treatment planning. The planning and implementation of radiation therapy that takes an hour or more using prior art procedures can be performed in much less time by use of the invention. This results in greater patient through-put and, perhaps more importantly, allows greater precision in therapy planning.

The invention utilizes differential scatter-air ratios to determine scatter contributions to total dose, but in a way that maximizes speed in dose calculation. Whereas in the prior art, dose calculations are based upon lengthy polar coordinate integrations, the present invention uses rectangular coordinate integrations which can, to an extent, be precalculated outside an integration loop.

In accordance with the invention, total radiation dose for therapy treatment is calculated by combining primary and secondary dose contributions from a radiation source to a specific region within the patient. The scatter contribution is calculated by integrating scatter contributions for other regions within the patient. A differential scatter-air ratio method is used where differential scatter-air ratios for radial distances within a plane of the patient are stored in a one dimensional matrix and a differential scatter-air ratio contribution for each subregion within the plane is accessed by converting a two dimensional coordinate within the plane to an offset or position within the one dimensional matrix.

Through an interactive process similar to that conducted in the prior art, a therapist plans a radiation treatment. The use of a two dimensional coordinate for determining an offset into the one dimensional matrix speeds integrations for the scatter component of the dose calculation. This procedure also results in a reduction in memory required to perform the scatter calculation.

In accordance with a preferred embodiment in the invention the calculation is performed in rectangular coordinates. In the prior art, the calculation was performed in polar coordinates so that for each boundry point of a beam configuration a new differential scatter-point air ratio figure was required, scatter contributions for a rectangular sequence of elements allow offsets into the one dimensional array of differential scatter-air ratios to be precalculated. Stated another way, differential scatter-air ratios for regions within a plane are precalculated in advance and then a rapid integration scatter summation performed by a computer for each subregion within the plane.

In accordance with another aspect of the invention, a beam profile matrix takes into account beam geometries built into the therapy plan by the therapist. Wedges, blocks, etc. used to define the radiation beam have an effect on both primary and scatter contributions to the region of interest. The primary effect due to these beam defining elements is precalculated and used to generate a one dimensional beam transmission matrix. Values for this matrix are convolved with the scatter contribution of a given region to correct for beam inhomogenieties. By reviewing the two aforementioned prior art publications, one sees that beam irregularities are ineffectually taken into account by the prior art and lengthen an already slow calculation.

One object of the invention is a rapid method of determining scatter contributions during a therapy planning session. This method uses the differential scatter-air ratio calculation procedure of the prior art but in a much more effecient manner that speeds the interactive planning process of the therapist. This and other objects, advantages and features of the invention will become better understood when a detailed description of a preferred embodiment of the invention is described in conjunction with the accompanied drawings.

BEST MODE FOR CARRYING OUT THE INVENTION

Figure 1:
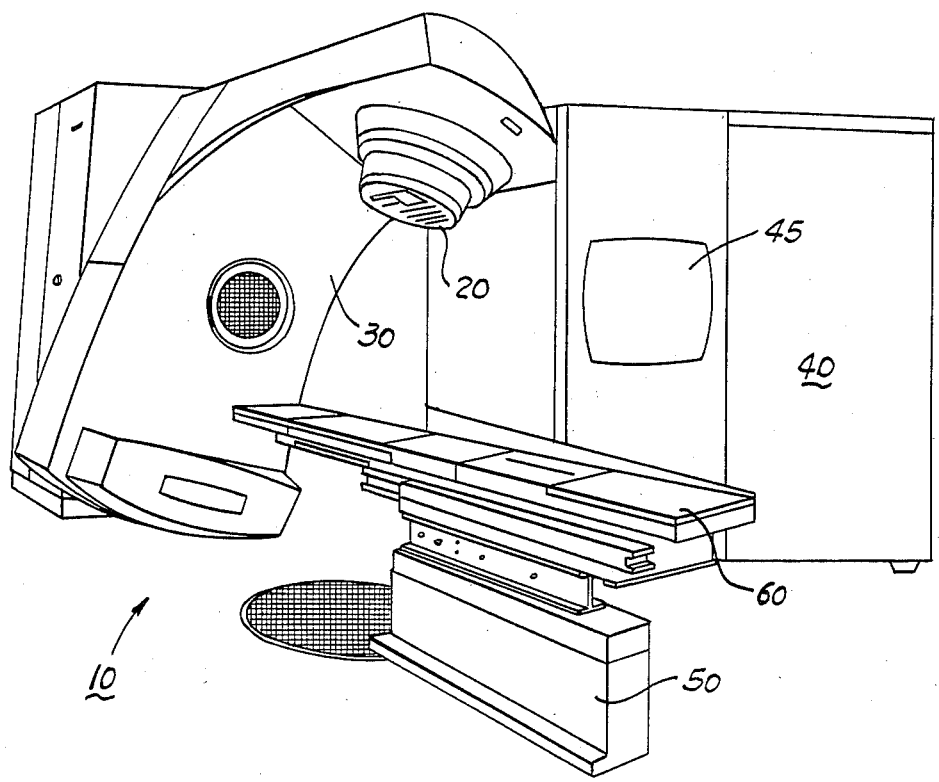
FIG. 1 is a schematic perspective view of a radiation treatment accelerator.

Referring now to the drawings, FIG. 1 depicts a radiation accelerator 10 including a radiation source 20 for irradiating a patient. The source 20 is mounted to an accelerator gantry 30 that rotates the source relative the patient. During treatment, the source 20 irradiates the patient in a manner such that x-radiation passes into the patient and is absorbed by patient tissue. Radiation treatment is performed using both gamma radiation from a radioactive source such as cobalt and can similarly be accomplished by x-radiation treatment from the accelerator 10. The discussion of a preferred radiation dose calculation procedure will be described in conjunction with x-radiation treatment but it should be appreciated that similar steps are utilized when utilizing radioactive materials.

A computer 40 helps a radiation therapist plan a treatment session. A mapping of radiation dose in a paitent cross-section is displayed on a cathode ray tube 45 to help the radiation therapist determine radiation dose within the patient.

A patient couch 50 helps position the patient relative the x-ray beam. A top 60 can be moved relative the source 20 to precisely position a particular patient cross-section within a radiation beam.

Once a tumor or cancerous region within the patient has been identified using a computed tomography or nuclear magnetic resonance scan, the radiation treatment therapist must plan a therapy session whereby specific doses of radiation are directed at the cancerous tissue in an effort to fatally damage the tumor while leaving other regions of the patient relatively unaffected.

Figure 6:
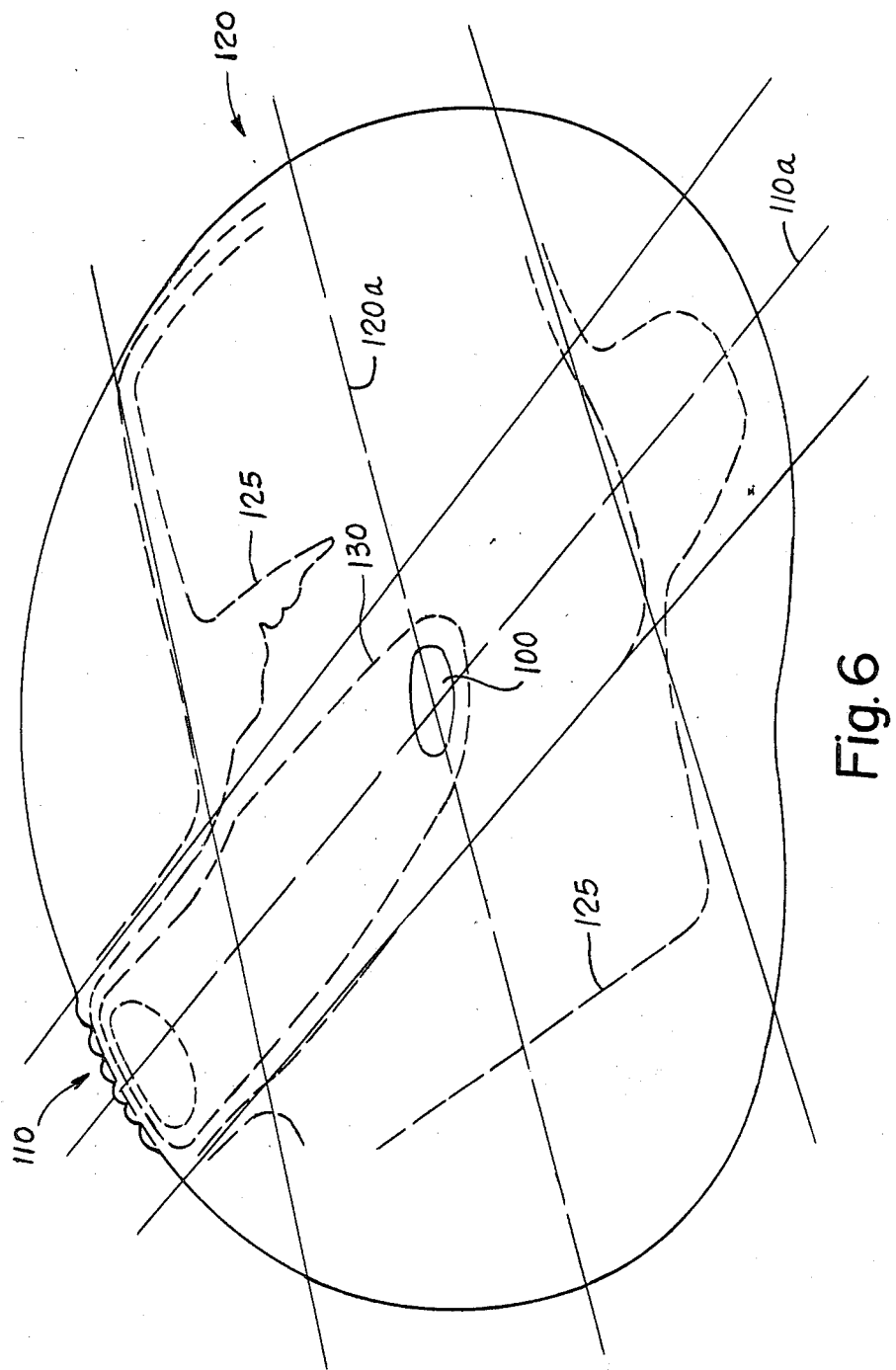
FIG. 6 is a view of a patient cross-section showing radiation impinging from two directions and mappings of isodose regions in the cross-section.
Figure 7:
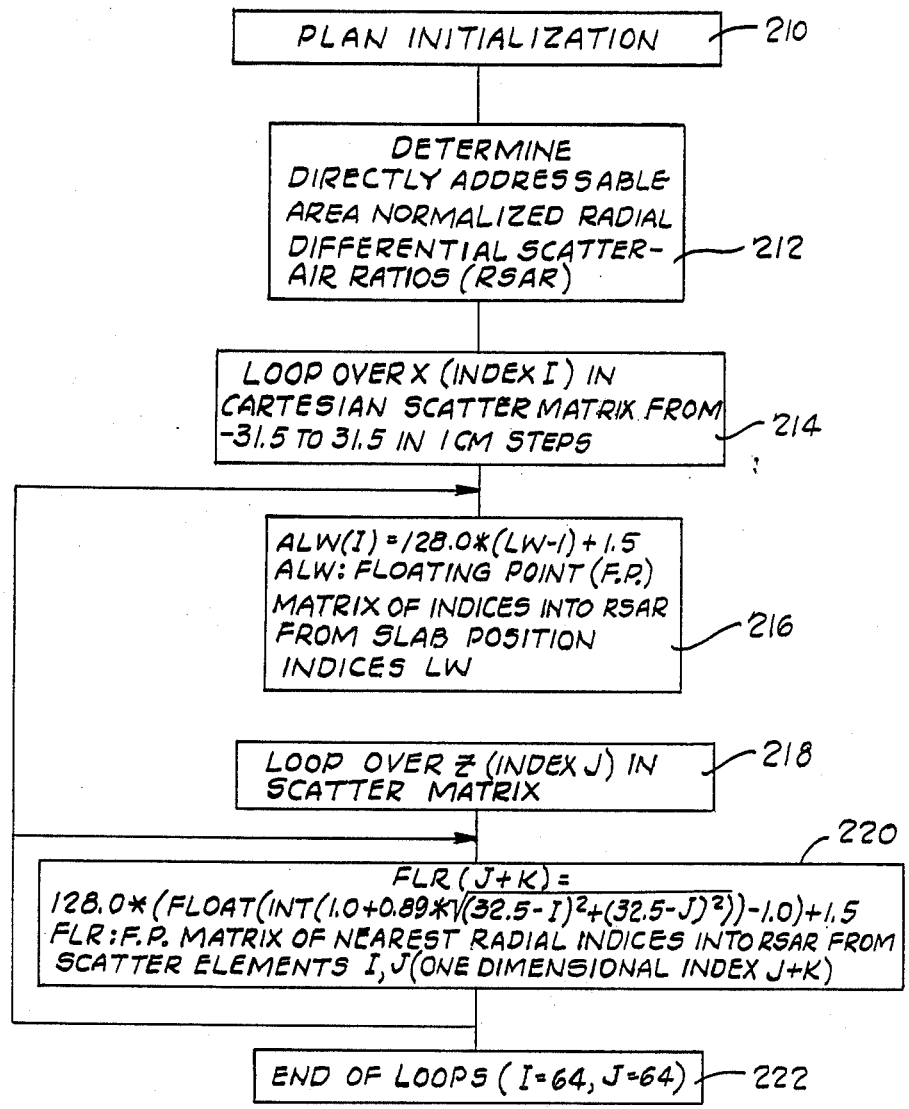
FIGS. 7 and 8A-8E are flowcharts of method steps for calculating radiation dose.

By way of introduction, a cross-sectional image of a patient region is illustrated in FIG. 6. This region includes a cancerous tumor schematically illustrated by reference character 100 that has been identified by the diagnostician from three dimensional computed tomography scans of the patient. Accepted treatment indicates a dosage of X rads of radiation when directed at the center of this tumor will have the therapeutic effect of fatally damaging the tumor 100.

Two oblique x-radiation beams 110, 120, having centerlines 110a, 120a, are seen impinging upon the tumor from different directions. The beams 110, 120 have different beam widths as generated by beam defining structure mounted relative the radiation source 20. The two beams 110, 120 are generated at different times. The patient is moved relative the accelerator gantry 30 until a particular cross-section, including the tumor 100, is positioned properly and the source 20 rotated about its circular path until it coincides with a position for generating the first beam 110. The patient is irradiated with the first x-ray beam 110 for a first time period and then the source 20 is rotated to a position such that the beam 120 is produced. The patient is then irradiated for a second period. To produce the total dose of X rads, the patient is typically radiated a number of times over an extended time period so that in a given session less than the total dose is received.

Prior to this radiation treatment, the x-radiation therapist must plan the irradiation sequence. To facilitate this planning, an interactive dose calculation procedure is followed, whereby the diagnostician chooses certain parameters and the computer 40 utilizes these parameters to produce a dosage mapping for patient regions. The radiation dose depends upon a number of variables, and in particular, varies with the depth of the region within the patient, position within a cross-section perpendicular to the x-radiation beam, patient contour at the region of x-radiation impingement upon the patient, x-radiation intensity, and position and orientation of various beam defining apparatus such as blocks (total or nearly total attenuation) and wedges (partial attenuation). The computer 40 must account for each of these variables in calculating patient dose and must do so as rapidly as possible.

Figure 2:
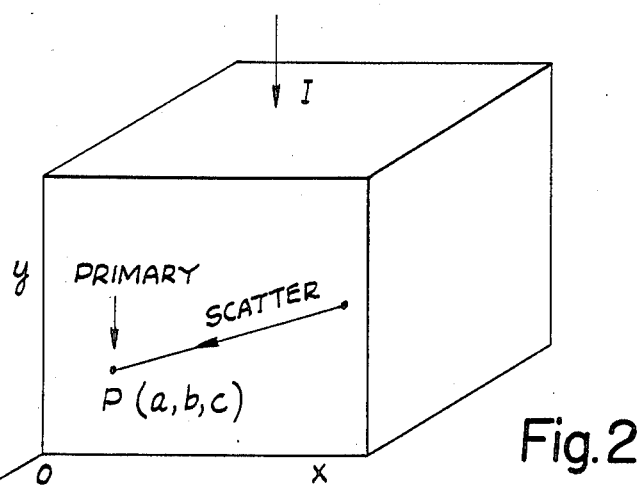
FIG. 2 is a perspective view of a representative slice of tissue with radiation impinging upon it.

FIG. 2 shows a perspective view of a representative volume of patient tissue having x-radiation impinging upon the volume parallel to a "Y" axis. The calculation of radiation dose for a particular point P having rectangular coordinates i, j, k relative a coordinate system origin 0 is conducted using the differential scatter-air ratio technique proposed and discussed by Cunningham in his prior art publications. The radiation dose is divided into primary and scatter contributions. The primary dose depends upon the x-radiation intensity from the source 20 and the attenuation the radiation experiences passing through the patient prior to reaching the point P. This is affected by patient contour and in calculating primary dose contributions it is assumed a uniform patient density is encountered once the x-radiation enters the patient. This primary dose calculation is also affected by the presence of radiation defining wedges and blocks, but so long as these contributions to radiation strength or intensity are known, the primary dose calculation is straightforward and can be quickly calculated by the computer 40.

As noted by Cunningham, the total dose calculation for the point P is also dependent on a scatter contribution resulting from radiation scattering from other regions within the patient to the point P. As pointed out by Cunningham, this scatter contribution can be computed with the aid of a computer using a summation technique which approximates an integration. Refering to FIG. 5, Cunningham's prior art technique of summing scatter contributions relative to the point P will be summarized and can be reviewed in detail in the referenced and incorporated prior art publications to Cunningham.

Figure 5:
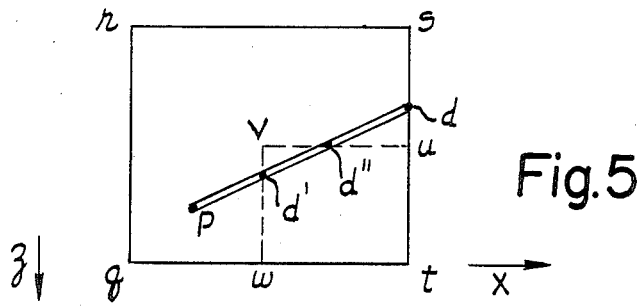

In FIG. 5, the radiation is directed perpendicular to the planar section illustrated. As a first example, consider a situation in which a uniform intensity beam forms a rectangle bounded by the four points q, r, s, t. In accordance with the Cunningham procedure, scatter contribution for regions within the patient volume (FIG. 2) are calculated using a summation technique wherein pie-shaped regions of radiation scatter are added together to form a total scatter dose. One such pie-shaped region is shown having an apex at the point P and a boundry at the point d. The pie-shaped region illustrated contributes a scatter dose to the point P given by the relationship:

$$S = S(d, r_e) \Delta \theta_e / 2\pi$$

where:
 d = depth within tissue to point;
 $r_e$ = distance from point to boundary of pie-shaped slice;
 $\Delta \theta_e$ = angular extent of slice; and
 S (d, $r_e$) = scatter-air ratio from look-up table.

To calculate the scatter contribution for the entire rectangle q, r, s, t, similar pie-shaped regions from the boundry of the rectangle to the point P are calculated and summed to produce a scatter contribution which is added to the primary contribution to produce a total dose. This procedure becomes particularly involved when blocks or wedges affect the total dose impinging upon the region. Stated another way, when a nonuniform radiation is used for therapy treatment, the differential scatter calculations become not only a summation of positive terms but a subtraction for regions irradiated with a nonuniform intensity. In FIG. 5, for example, when a block is inserted within the x-radiation beam to totally prevent primary radiation from reaching the rectangle defined by points t, u, v, w of the figure, the scatter contribution for the pie-shaped region extending from the point P to the point d must take into account this beam inhomogeneity. Cunningham suggests a subtraction of the scatter for the blocked off region extending from the two points d', d" in FIG. 5.

The prior art method of calculating scatter contribution is inefficient since a new differential scatter-air ratio S (d, $r_e$) for each point along the rectangle perimeter q, r, s, t must be determined for each pie-shaped segment. This is a time consuming operation for the computer and results in long calculation times which adversely affect patient throughput. The scatter calculations of the present invention will be described in overview with respect to FIGS. 3 and 4 and described in more detail in the flow charts of FIGS. 7 and 8A-8E.

Figure 3:
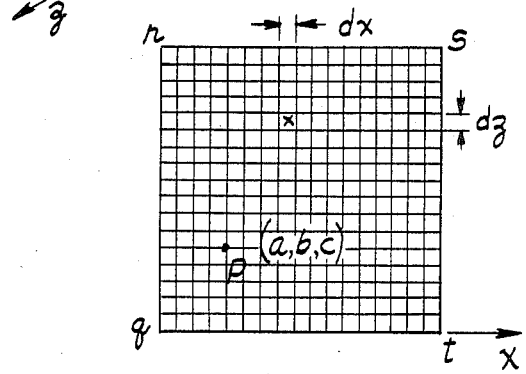
FIGS. 3-5 are plan views of the FIG. 2 tissue showing certain features of a radiation dose determination.

Turning to FIG. 3, the rectangular region q, r, s, t of FIG. 5 has been reproduced showing the calculation point P. As in the prior art, the present method breaks the dose contribution in two parts. The primary calculation is performed and a scatter contribution added to produce a total dose for a particular subregion P within the patient. For the point P, each of the rectangular elements dx, dz (FIG. 3) contributes to scatter dosage. In accordance with the present invention, the scatter contribution for each small region dx, dz is summed in a iteration loop by the computer 40 by accessing a table of radial scatter-air ratios (RSAR) that have been precalculated based upon initial parameters such as radiation intensity. The calculation of the dose at point P involves a summation of all small elements dx, dz shown in FIG. 3. In accordance with one procedure, scatter contribution for each element within a row is calculated in turn and then the row is indexed until the scatter contribution for an entire region bounded by the points q, r, s, t has been calculated. In a disclosed and preferred embodiment, the dimensions dx, dz are one centimeter and a particular plane within the patient is divided into a grid matrix of these one centimeter square elements.

The specifics of a calculation involve determining the radial distance from the point P to the point dx, dz and determining an offset into the one dimension radial scatter-air ratio matrix that points to a value which is added to the scatter contribution for the point P. This one dimensional radial matrix is precalculated based upon the beam characteristics chosen by the therapy diagnostician.

Each region dx, dz within the rectangle q, r, s, t has an offset into the one dimensional radial scatter-air ratio matrix. The memory requirements for storing the one dimensional matrix are an order of magnitude less than the requirements for storing a scatter-air ratio for each element dx, dz in the plane. In a representative dose calculation where dose to a 128×32×32 centimeter patient region is determined this storage savings (assuming 1 cm increments in calculations) reduces the storage requirements from 524k bytes (128×32× =131,072) to approximately 32k bytes (128×64=8,192) if four bytes of data are stored per table entry.

Once an entire plane of dose values are calculated, the y dimension is indexed and doses are calculated for each other slab or patient cross-sections perpendicular to the radiation I.

If more than one radiation beam (FIG. 6) impinges on the patient, the dose contributions to a point P must be combined for a total dose mapping for the entire patient region of interest.

Figure 4:
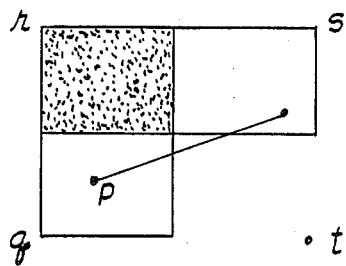

Turning to FIG. 4, the uniform rectangular radiation pattern of FIG. 3 is modified using a block which completely attenuates radiation from passing to a quadrant of the rectangular region. A second region identified with stipling is a region where a wedge has been used to attenuate radiation passing through the patient but wherein the wedge has a transmission factor which allows a certain percentage of radiation to impinge upon the patient.

The Cunningham procedure of selectively subtracting scatter contributions based upon inhomogeneities in the radiation pattern impinging on the patient is replaced in the invention by a procedure wherein the modified intensity is made part of a one dimensional transmission matrix in advance of the computer summations. Both scatter and primary dose to the point P take into account the different beam intensities impinging upon the region q, r, s, t stored in this matrix.

FIGS. 7 and 8A–8E illustrate a preferred implementation of the dose calculations of the invention. In the algorithms discussed in FIGS. 7 and 8A–8E, a reference system consistent with that defined in FIGS. 2–5 is used in calculating radiation dose. In the frame of the patient, the positive X direction is to the right looking towards the paitent's head, the positive Y direction is towards the patient anterior or front and the positive Z direction is towards the patient's feet.

A plan initialization step 210 (FIG. 7) is an interactive process with a computer 40, wherein the user enters various specification data to determine parameters for the dose calculation. Certain of these parameters are available from the three dimensional computed tomography scan, for example, the patient contour can be accessed by the computer 40 based upon an initial patient scan.

At step 212 (FIG. 7), a process of obtaining radial indices as a function of scatter point coordinates begins. Returning to FIG. 3, each representative area dx, dz can be characterized as an offset into a one dimensional radial scatter-air ratio matrix so that once one knows the X and Z coordinates of the point, one can directly access a location in that matrix. The steps 214, 216, 218, 220 represent the generation of a matrix FLR indicating an offset for a particular X and Z coordinate (I and J in a FORTRAN implementation of the flowchart). The two loops 214, 218 index the X and Z coordinates within a plane (constant Y coordinate). For each X and Z combination an entry in the matrix FLR is calculated. The formula in method step 220 is the FORTRAN representation of the pythagorean theorem for the initial conditions defined in step 210. As seen in method step 222, the calculation loops end when radial offsets for a 64 by 64 array of elements dx, dz (FIG. 3) has been calculated so that for each coordinate within the plane an appropriate address into the matrix FLR is determined. This address stores an offset into RSAR, a radial scatter-air ratio matrix to be calculated below.

Figure 8A:
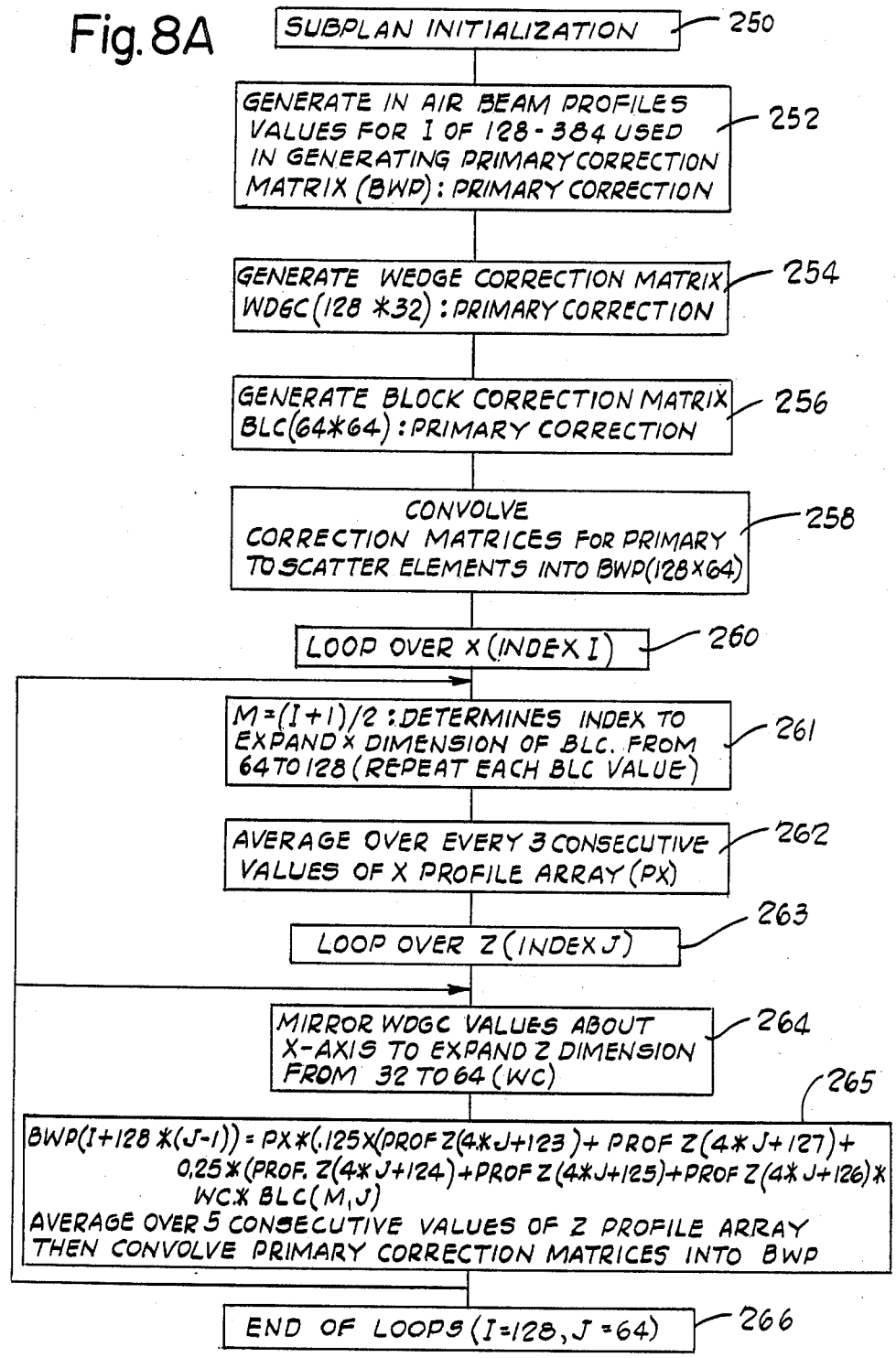

Turning now to FIG. 8A, the algorithms for calculating dose to a particular point are discussed. The theory of calculation separates the scatter and primary contributions which are added at the end of the calculation. This algorithm begins with an initialization step 250 which primarily relates to parameters defining the beam for which the dose calculation must be performed. The beam is defined in terms of coordinates within the X, Y, Z reference frame at which the beam intersects the surface of the patient, the limits of the beam as defined by a beam defining apparatus (not shown) and the orientation of the patient. Additionally, the initialization step 250 includes information relating to beam intensity including inhomogeneity in that intensity due to the existence of blocks and wedges placed in the beam path between the x-ray source 20 (FIG. 1) and the paitent. At a next step 252, a primary dose matrix BWP for each point in the region of the beam bounded by inside edges of a beam penumbra is generated. This matrix is an initial primary dose matrix used as a starting point for dose calculations. A next step 254 in the FIG. 8A algorithm corrects the primary matrix based upon wedge information since the presence of a wedge defining member in the beam path affects the primary at certain points within the beam cross-section. In the FIG. 4 representation, the beam quadrant that is attenuated (stipled) has a transmission factor entered into a matrix WDGC to account for this attenuation.

At a next step 256 in the algorithm, a block correction matrix BLC is generated based upon the presence of beam blocking apparatus inserted into the x-ray beam. At a next step 258 the three matrices generated in the previous steps 252, 254, 256 are convolved into a single matrix BWP for scatter calculations. This is accomplished in the remaining method steps 260–266 in FIG. 8A. The matrix BWP is a one dimensional matrix formed from the initial BWP matrix 252, the wedge WDGC matrix 254 and the block correction matrix BLC 256. The value of BWP for a given X, Z coordinate (I, J index in FORTRAN) is a beam profile at the region X, Z. Subsequent to the step 266, the computer has defined the beam in terms of the output from the x-ray tube, beam blocking geometry and any wedges inserted within the beam.

A tissue-air ratio DNOR for a normalization point is calculated at a next step 270 (FIG. 8B) in the dose calculation algorithm. This reference tissue-to-air ratio is based upon the beam characteristics and is used as a reference dose to which the remaining points in the region under scrutiny are referenced. DNOR is calculated in accordance with Day's method for calculating dosage at any depth within a rectangular beam.

At a next step 272, a contour correction matrix CCOR is generated. CCOR stores distances from points the beam enters the patient to a plane intersecting the point the beam center enters the patient. This data allows distances into the patient from a point of entry of the x-ray beam to dose calculation points to be determined. This distance is used in generating scatter-air ratios in accordance with the Cunningham technique.

Figure 8B:
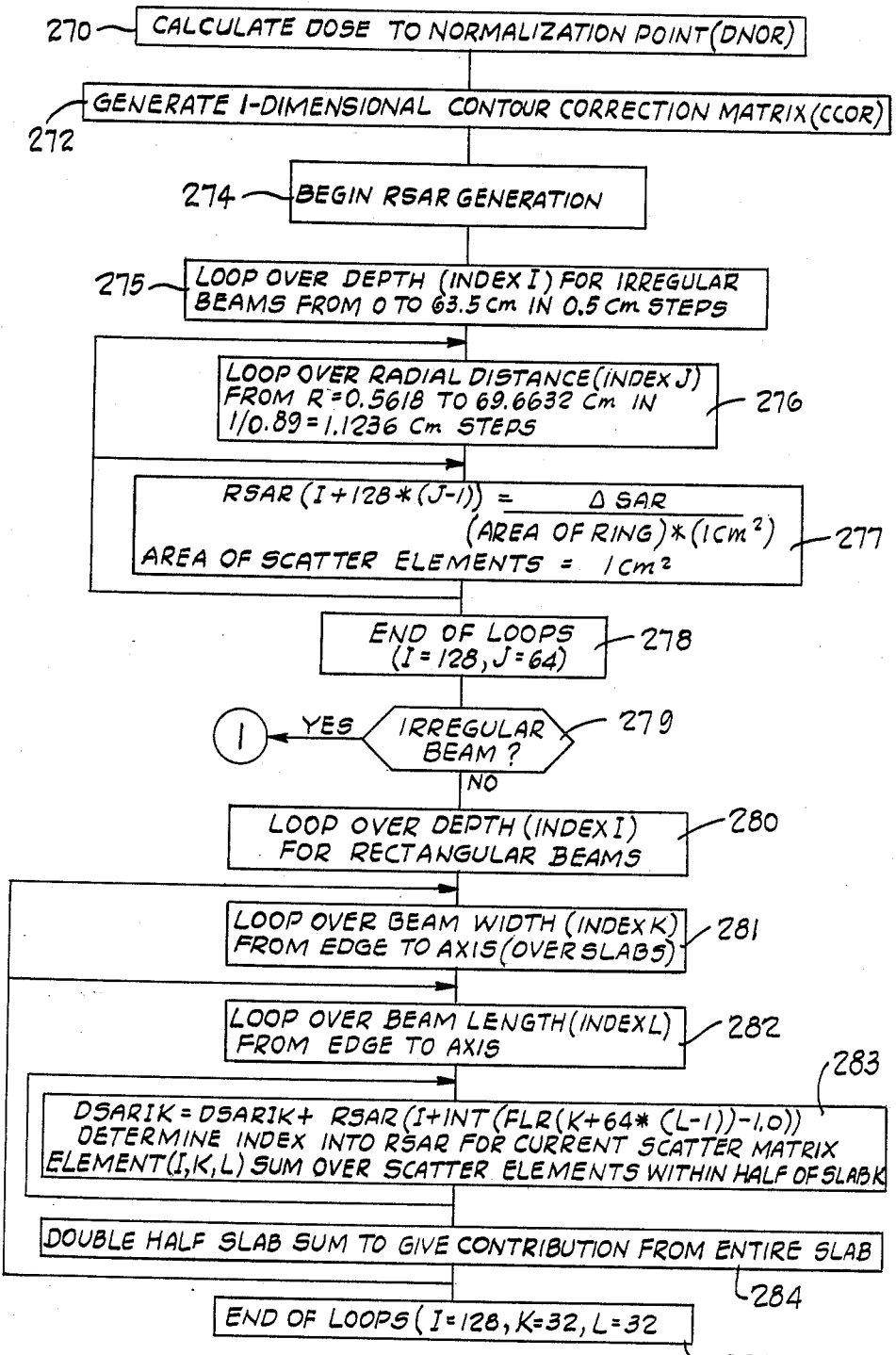
Figure 8C:
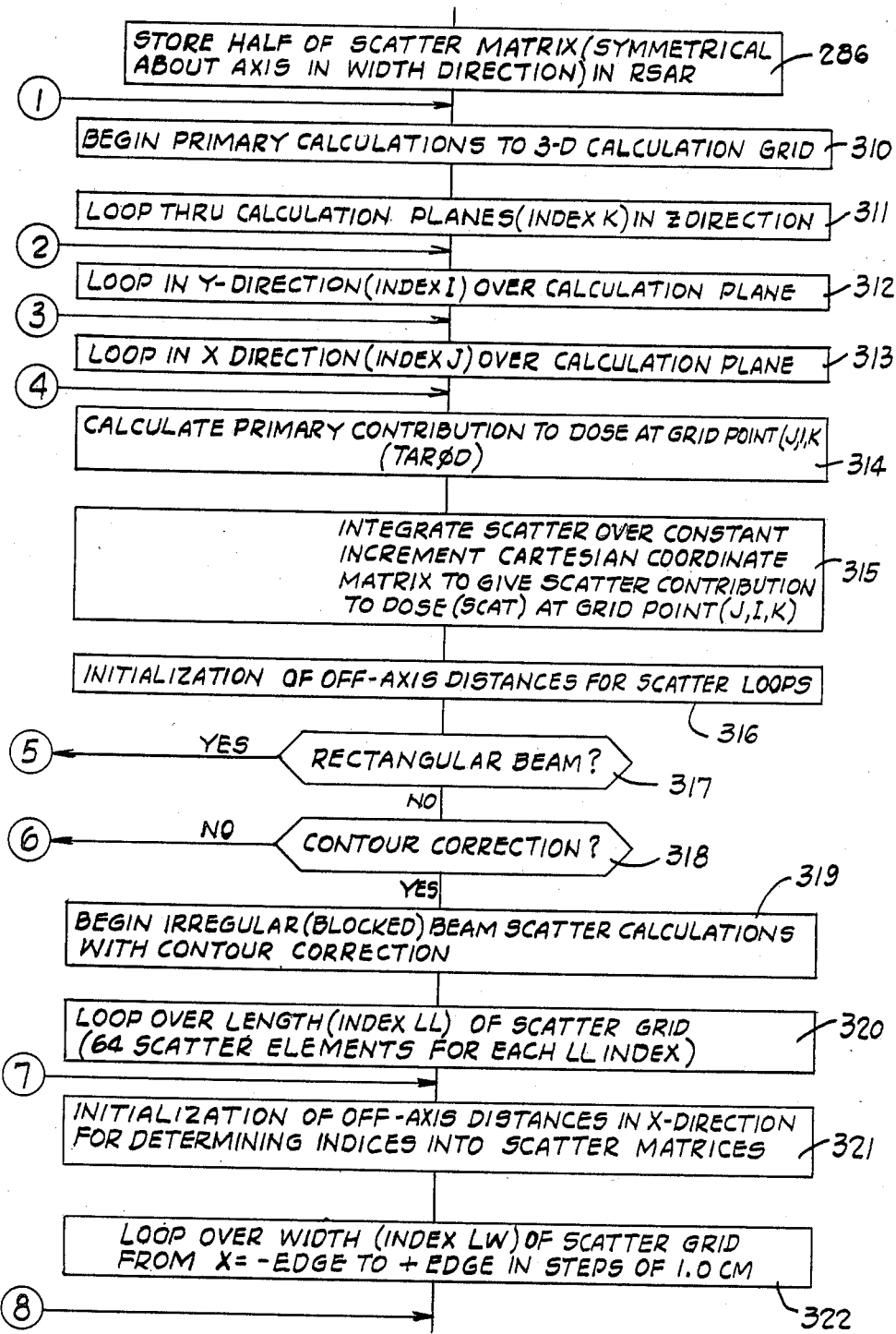
Figure 8D:
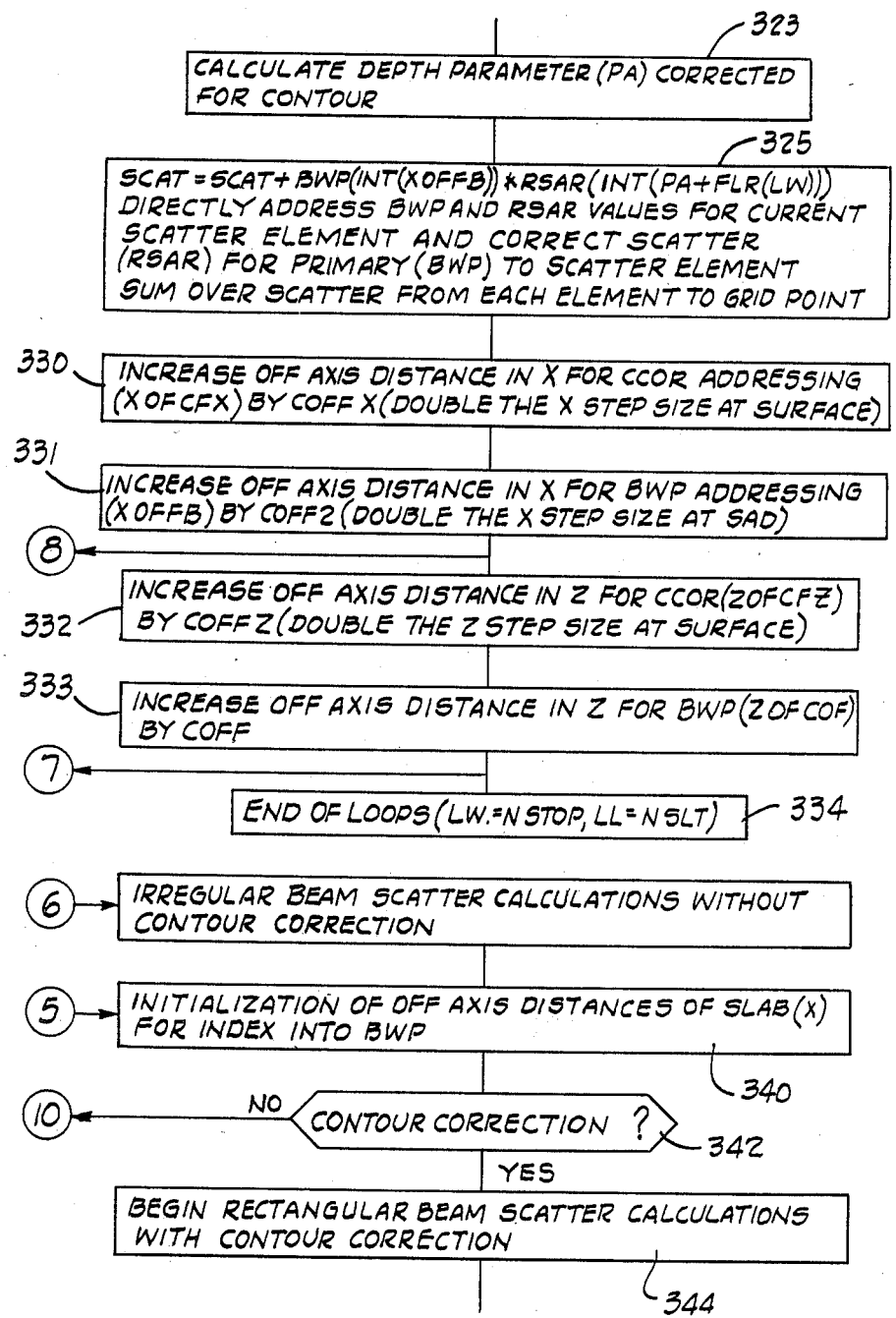
Figure 8E:
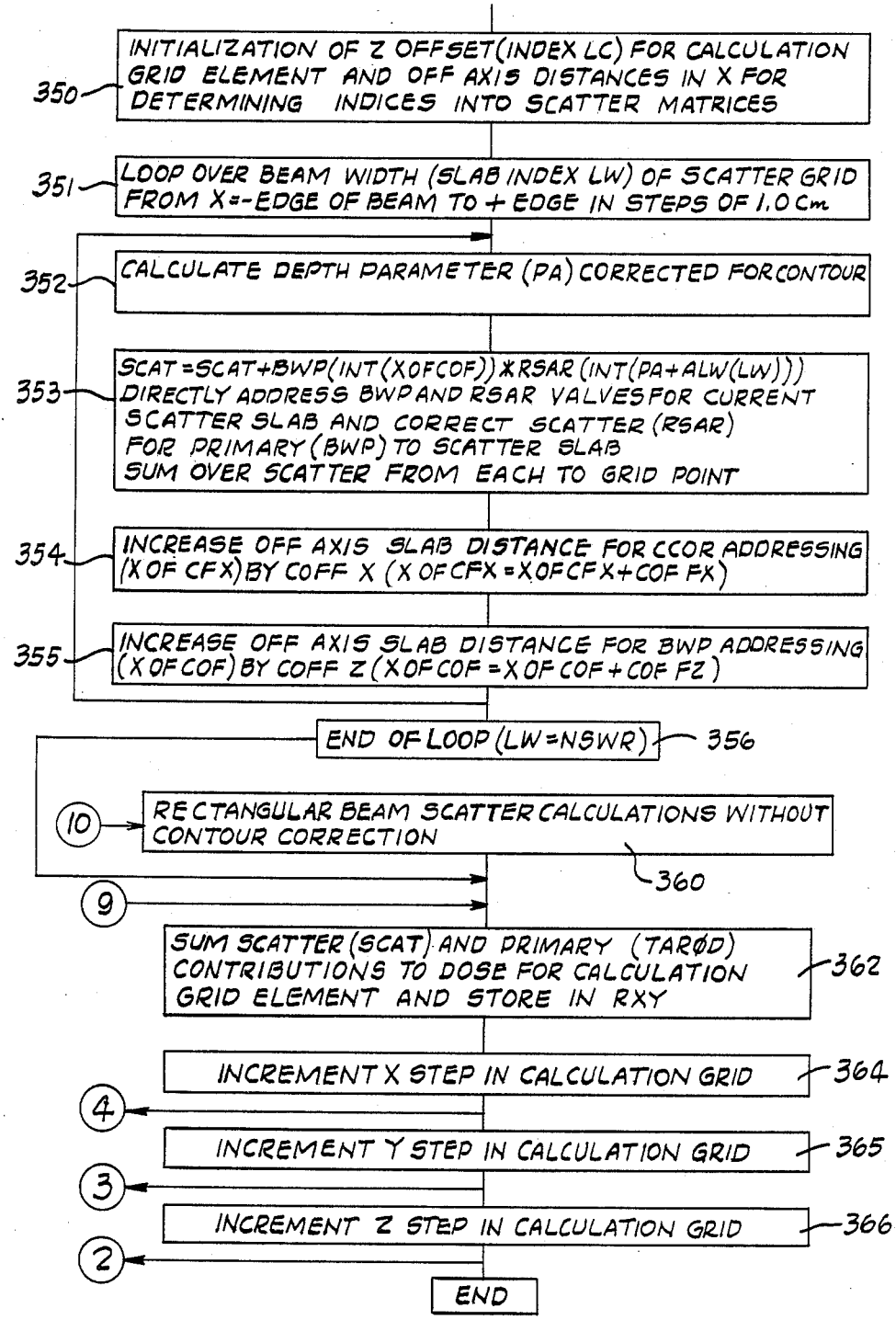

Radial scatter-air ratios (RSAR) are generated in the steps 274–278 in FIG. 8B. Scatter-air ratios (SAR) for a particular depth within the patient are used to generate the radial scatter-air ratios (RSAR).

In these RSAR calculations the index J corresponds to a radial distance from a calculation point to a scatter point and the index I corresponds to a depth within the patient. These indexes refer only to the steps 274–278.

The calculation at method step 277 is a determination of the radial scatter-air ratios as a function of depth and radial distance. RSAR is the difference between the scatter-air ratio for the radius J and the scatter-air ratio for the radius J+1 divided by the area of the ring encompased by circles having the radii J and J+1. The scatter-air ratios SARs are known values read into computer memory at the initialization step 250.

The algorithm next determines 279 if the radiation beam is rectangular and symmetric about the z axis. If the beam is not symmetric, the computer skips to FIG. 8C and primary dose calculations begin. If the beam is symmetric and uniform about the z axis, the scatter dose is the same for elements symmetric with respect to the z axis and a simplification in the RSAR matrix is performed at steps 280–286. This simplification precalculates scatter for a slice parallel to the z axis so that during a scatter summation, the scatter to a given point is conducted by summing across the beam width.

Method steps 310-313 (FIG. 8C) begin the dose calculations in the x, y, z coordinate space with calculation loops that access each point in each calculation plane. At step 314 the primary dose TAROD for each calculation point J, I, K is determined. At the next step 315, the scatter contribution at the point is determined using a constant increment cartesian coordinate summation.

The scatter calculation begins with calculations 316 of distances of the point J, I, K from the x, y and z axes. This sets the limit for integration for each point. Two decision steps 317, 318 determine the parameters of the scatter calculation in terms of beam geometry and whether a contour correction is to be performed. Step 319 indicates a blocked beam with contour correction scatter calculation is performed.

Steps 320-322 set up a rectangular coordinate integration where scatter contributions of each point dx, dz (FIG. 3) for the beam geometry are added in turn until a total scatter contribution is determined.

Since contour correction is performed, the depth (PA in the flow diagram) from the point the beam enters the patient to the integration point dx, dz is calculated 232. The next step 325 is the scatter calculation. In the equation of step 325 (FIG. 8D) the incremental scatter from the region dx, dz is determined by the three variables XOFFB, PA, and LW. PA is the depth variable in the RSAR table and LW is the radial distance from the point J, I, K to the region dx, dz. XOFFB is an offset into the matrix BWP (calculated at step 265) based upon the position of the incremental region dx, dz within the beam.

The calculation of the three variables XOFFB, PA, and LW is straightforward yet powerful. These variables are well ordered and not susceptible to the lengthy calculations involving complex exponential terms necessary in the prior art. The matrix BWP defines the beam characteristics so that multiplication of the BWP matrix element with the RSAR value convolves the scatter characteristics of the beam into the region dx, dz RSAR value.

After the scatter contribution SCAT for the region dx, dz is added, the loop variables are incremental 330-333 until the scatter contributions for all incremental regions in the plane of the point J, I, K have been summed 334.

Returning to FIG. 8C, at decision step 317, had the beam been rectangular, a branch to step 340 (FIG. 8D) occurs. At step 342, the decision step (318) regarding the contour correction is made and at the next step 344 a rectangular beam scatter calculation with contour correction is made.

Method steps 350-356 correspond to the scatter calculation steps discussed above, but for a rectangular beam. The computer only loops over the beam width since the RSAR table for a rectangular beam already includes the scatter contribution to the point J, I, K from a lengthwise slice (see step 283) a given perpendicular distance from the point at specified depths within the patient. By looping across the beam width and changing only the primary offset XOFCOF and the contour correction variable PA the scatter calculation is simpler and faster for the rectangular beam.

To obtain a rapid dose calculation, the therapist may wish to obtain a dose mapping without patient contour correction or the use of blocks and wedges. This choice at step 342 (FIG. 8D) causes the computer to calculate dose for a rectangular beam with no contour correction. This condition causes the computer to branch to this calculation 360 for each point J, I, K.

To complete the calculation, the primary and scatter doses are added 362 and stored in memory. At steps 364-366, the J, I, K variables of regions within the patient are indexed and radiation dose for other regions calculated and stored in memory. These values are used to create the mapping of FIG. 6 on the cathode ray tube 45 as an aid to the therapist in planning a patient treatment.

Turning to FIG. 6, the tumor 100 is intersected by the two beam centerlines 110a, 120a. One isodose delineating indicator 130 of an intensity of $x \div n$ rads is bounded by other isodose indicators 125 of lesser intensity. By modifying the beam geometries the therapist can more nearly isolate the indicator 130 about the tumor 100 to minimize dose to other regions. The new and improved dose calculation embodied by the FIGS. 7 and 8A-8E flow diagram increase the speed of this process by rapidly presenting a mapping similar to FIG. 6 as the beam geometry is altered. The equal increment integration (summation) of the disclosed method suggests the possibility of implementing the scatter loop using an array processor to decrease the calculation time even further, potentially by an order of magnitude.

The flow diagrams discussed above represent FORTRAN implementation of the improved dose calculations. The steps of convolving beam characteristics into the scatter and printing calculations, use of a well ordered summation for incremental regions within the body, and the data organization using radial scatter-air ratios in a one dimensional matrix of values for each beam geometry can be implemented using other languages. The method also has applicability to electron rather than photon beam calculations. Although the disclosed implementation has been described with a degree of particularity, it is therefore the intent that the invention include all alterations and modifications falling within the spirit or scope of the appended claims.

We claim:

1. A method of determining radiation dose for therapy treatment of a patient comprising the steps of:
   calculating a primary dose contribution from a radiation source to a region of said patient;
   calculating a scatter dose contribution to said region for radiation scattered from other regions within said patient by a differential scatter-air ratio method where the differential scatter-air ratios for subregions within a plane of the patient are stored in a one dimensional matrix and a differential scatter-air ratio for each subregion within the plane is accessed by converting a two dimensional coordinate within the plane to a position within the one dimensional matrix;
   combining the primary and scatter contributions to provide a total patient dose to the region; and
   mapping radiation dose over a region of the patient to aid in planning a radiation treatment.

2. The method of claim 1 wherein said scatter dose calculation step comprises calculating the scatter dose contributions of subregions within the plane in turn, according to a rectangular coordinate sequence and where each subregion has a corresponding differential scatter-air ratio in the one dimensional matrix.

3. The method of claim 2 comprising the additional step of determining doses for multiple planes and using said determined doses to generate a three dimensional mapping of radiation dose.

4. The method of claim 1 wherein said combining step comprises calculating the scatter contribution from the one dimensional matrix of differential scatter-air ratios and weighing each ratio to account for radiation beam inhomogeneities at the scatter subregion.

5. The method of claim 1 wherein the radiation is generated by a source of x-radiation.

6. A therapy planning method for radiation treatment of cancerous tissue by irradiation of the tissue with an optimum radiation dose comprising the steps of:
   estimating a radiation plan to produce said optimum dose, said estimated plan defining a radiation beam geometry;
   determining primary radiation dose to the patient based on the beam geometry;
   calculating scatter-air ratios based upon the beam geometry to produce a radial scatter-air ratio table;
   iteratively determining scatter dose to subregions within the patient by calculating radial distances from a subregion to irradiated points within the patient and attributing a scatter contribution from the radial scatter-air ratio table to each of said irradiated points for each subregion;
   combining scatter and primary dose to each subregion to produce a total dose mapping for the irradiated portion of the patient;
   comparing the dose mapping with the optimum dose for said tissue; and
   adjusting the radiation beam geometry to match the optimum with the calculated total radiation dose.

7. The planning method of claim 6 comprising the step of previously defining the beam geometry by use of blocks and wedges and convolving the effect these blocks and wedges have on scatter into the scatter contribution from each irradiated point.

8. The method of claim 6 where said iterative determination step comprises carrying out in successive patient planes and for each plane rectangular coordinate integration for incremental rectangular portions of the plane.

9. The method of claim 7 wherein said convolving step comprises calculating the beam characteristics at a particular point within the beam cross-section and made part of a one dimensional beam defining matrix that issued in convolving the beam characteristics onto the scatter contribution from regions within the patient.

10. Apparatus for determining radiation dose for therapy treatment of a patient comprising:
    means for defining a radiation beam in terms of beam strength at locations within the beam;
    means for calculating a primary dose contribution from a radiation source to regions within said patient based upon beam strength data from the means for defining;
    means for calculating a scatter dose contribution to said region for radiation scattered from other regions within said patient by sequentially determining differential scatter-air ratios for incremental subregions within each plane of the patient by accessing data stored in a one dimensional radial scatter-air ratio matrix for radial distances within the plane by converting a two dimensional coordinate of the incremental subregion to a position within the one dimensional radial scatter-air ratio matrix;
    means for combining the primary and scatter contributions to provide a total patient dose to said regions; and
    means for displaying a mapping of radiation dose to said regions.

11. The apparatus of claim 10 wherein the means for calculating scatter dose contributions of incremental subregions within the plane follows a rectangular coordinate sequence and where each subregion has a corresponding scatter-air ratio in the one dimensional radial scatter air matrix.

12. The apparatus of claim 10 where the means for calculating scatter dose includes means for convolving scatter contributions from incremental subregions with beam strength for the subregion from the means for defining to produce said scatter dose contribution.

13. A method of determining beam strength for a region within a patient comprising the steps of:
    calculating a primary beam contribution from a source to a region of said patient;
    calculating a scatter beam contribution to said region for beam portions scattered from other regions within said patient by a differential scatter-air ratio method where the differential scatter-air ratios for subregions within a plane of the patient are stored in a one dimensional matrix and a differential scatter-air ratio for each subregion within the plane is accessed by converting a two dimensional coordinate within the plane to a position within the one dimensional matrix;
    combining the primary and scatter beam contributions to provide a total beam strength at the region; and
    mapping beam strength over a region of the patient.

14. The method of claim 13 wherein said step of calculating the scatter contributions of subregions with the plane comprises calculating, according to in turn a rectangular coordinate sequence and where each subregion has a corresponding differential scatter-air ratio in the one dimensional matrix.

15. The method of claim 13 comprising the additional step of weighing the scatter contribution determined from one dimensional matrix of differential scatter-air ratios to account for beam inhomogeneities at the scatter subregion, as part of said combining step.

* * * * *